United States Patent [19]

Dretler

[11] Patent Number: 4,927,426
[45] Date of Patent: May 22, 1990

[54] CATHETER DEVICE

[76] Inventor: Stephen P. Dretler, 7 Deer Run, Wayland, Mass. 01778

[21] Appl. No.: 292,910

[22] Filed: Jan. 3, 1989

[51] Int. Cl.⁵ .............................................. A61B 17/22
[52] U.S. Cl. ..................................... 606/128; 604/280
[58] Field of Search ................... 604/21, 22, 164, 264, 604/271, 280, 281, 282; 606/127, 128; 128/749, 750, 752, 756

[56] References Cited

U.S. PATENT DOCUMENTS

| 2,943,626 | 7/1960 | Dormia | 606/127 |
| 4,198,960 | 4/1980 | Utsugi | 606/127 X |
| 4,299,225 | 11/1981 | Glassman | 606/127 |
| 4,611,594 | 9/1986 | Grayhack et al. | 606/127 |
| 4,625,726 | 12/1986 | Duthoy | 606/127 |
| 4,692,139 | 9/1987 | Stiles | 604/22 |
| 4,790,812 | 12/1988 | Hawkins, Jr. et al. | 604/22 |

Primary Examiner—Mickey Yu
Assistant Examiner—Beth Anne Cicconi
Attorney, Agent, or Firm—Fishman, Dionne & Cantor

[57] ABSTRACT

A catheter device for capturing and holding kidney stones and the like wherein the catheter is an elongated tube having a cuff portion disposed on one end thereof capable of being collapsed axially inwardly into the tube and a snare disposed and axially moveable within the catheter for capturing and holding a kidney stone and collapsing the cuff portion. The snare is a second elongated tube capable of receiving a laser fiber for disintegrating a kidney stone when captured and held by the snare.

9 Claims, 2 Drawing Sheets

CATHETER DEVICE

BACKGROUND OF THE INVENTION

This invention relates to a catheter means for capturing and holding kidney stones or similar objects in the urinary tract or other passages of the human body. Specifically, this invention relates to a catheter-like device having capturing and holding means at its distal end for enveloping a kidney stone or the like preparatory to disintegrating same by known lithotrity methods.

In the field of urology, it is sometimes necessary to enter the urinary tract or other passage of the human body in order to remove objects therefrom such as kidney stones and the like. In the case of kidney stones, they are usually found in either the urethra, bladder and/or the ureters.

While many devices, i.e. catheters, have been developed for the removal of said objects, said devices when used often bring about a scratching or injuring of the walls of said narrow body passages which is undesirable as such injuries may cause infections and irritations. A typical device for the removal of kidney stones and the like is disclosed in U.S. Pat. No. 4,243,040 to William H. Beecher.

In U.S. Pat. No. 4,243,040, there is disclosed a device which comprises a flexible inner tube and a flexible outer tube which are joined together at their distal ends by an inflatable sleeve. In using said device, the inner and outer tubes are inserted into a body passage such as the urethra to a point where they contact the object to be removed. With the tubes in such contact, a vacuum is applied to the inner tube in order to draw and hold the object against the end of said tube. With the object so held, the inner tube is retracted within the outer tube thus causing the inflatable sleeve to fold over the object as it is held by the inner tube. In this position, i.e. with the object at least partially covered by the inflatable sleeve, the device with the object held therein can be withdrawn from the body passage with a minimum of injury to the passage.

Rather than risk injury to the narrow body passages by using devices such as referred to above, it has been found that it is safer to disintegrate an object within a body passage and either actively remove the fragments or allow the passive removal of same by means of normal urinary function.

It is an object of the present invention to provide a catheter-like device for disintegrating kidney stones and the like within a body passage and for removing the fragments of said disintegrated stones.

It is another object of the present invention to provide a catheter-like device for capturing, holding and enveloping a kidney stone or the like preparatory to disintegrating same by known lithotrity methods.

It is a still further object of the present invention to provide a catheter-like device for disintegrating kidney stones and the like wherein said device does not employ liquid and/or gaseous fluids in the use thereof.

DESCRIPTION OF THE DRAWINGS

The above and other objects and advantages of the present invention will become more apparent from the following detailed description taken in connection with the accompanying drawings wherein:

FIG. 4 is a view similar to FIG. 3 showing the wire snare capturing a kidney stone or the like;

DESCRIPTION OF THE PREFERRED EMBODIMENT

Figure 1:
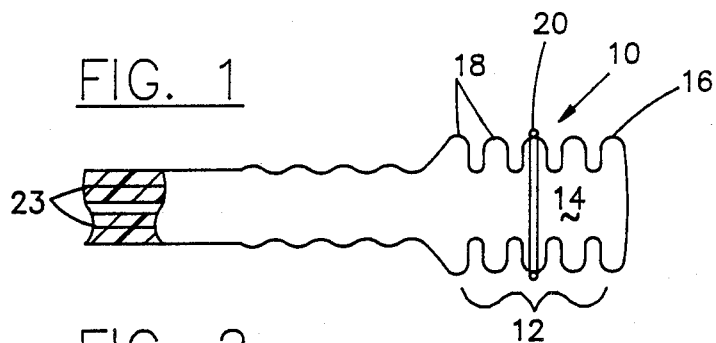
FIG. 1 is a side view of the catheter of the present invention having portions broken away.
Figure 2:
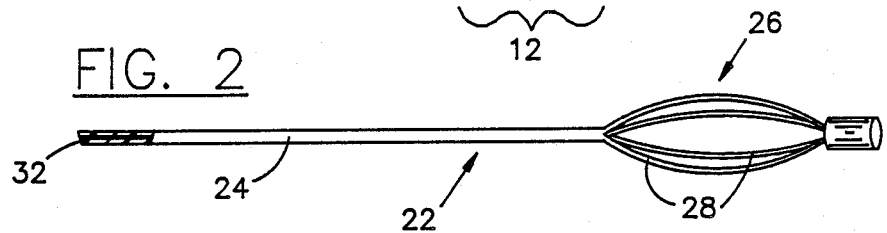
FIG. 2 is a side view of a wire snare used in association with the catheter of FIG. 1.

Referring first to FIGS. 1 and 2, the catheter of the present invention is shown at 10. The catheter 10 is essentially an elongated tube or cannula having an inwardly collapsable cuff portion 12 disposed at its distal end 14. In the cuff portion 12, the outer wall 16 of the catheter 10 is expanded so as to permit said portion to collapse axially inwardly. The cuff portion 12 may also be provided with corrugations 18 so as to provide more flexibility and aid in inward axial collapsing of the cuff portion 12. As also shown, a support means such as ring or band 20 disposed about the circumference of said flexible outer wall 16 and stiffening means 21 in the form of wire filaments 23 may be provided to aid in the collapse of the tube within itself as will be explained in detail below. As will be noted, said stiffening means is molded into the outer catheter wall 16 and extends up to the midpoint of the cuff portion 12. Said stiffening means 21 which comprises at least one wire filament 23 along with said support means 20 makes most of the catheter relatively stiff and therefore prevents the continued collapse of the cuff portion beyond said midpoint of said cuff portion 12.

As illustrated in FIGS. 2 thru 8, the catheter 10 is also provided with a snare means 22 as shown in FIG. 2. The snare means 22 is a stiff but flexible elongated tube 24 with a capturing head 26 disposed at the distal end. The filaments 28 which comprise the capturing head 26 are affixed to and disposed about the open distal end of the tube 24. This construction permits the insertion of an optical fiber 30 or other auxiliary device (see FIGS. 5 and 6) into the passageway 32 formed by the tube 24. When the snare means 22 is inserted into the catheter 10, it provides a means whereby the catheter 10 per se is stiffened thereby permitting easier insertion into a body cavity.

As stated above, the catheter 10 of the present invention is capable of being inserted into a narrow passage of the human body. Accordingly, said catheter 10 should be of such a length, for example, so as to enable it to be inserted into the urethra and the bladder and ultimately into one of the ureters.

Figure 3:
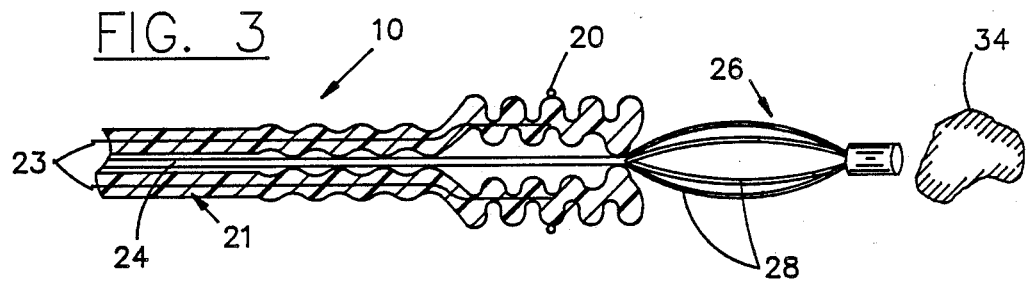
FIG. 3 is a side section view of the distal end of the catheter of the present invention showing the wire snare positioned for use therein.
Figure 4:
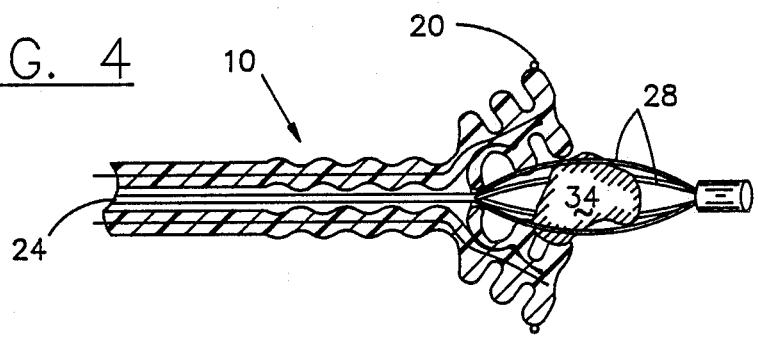
Figure 5:
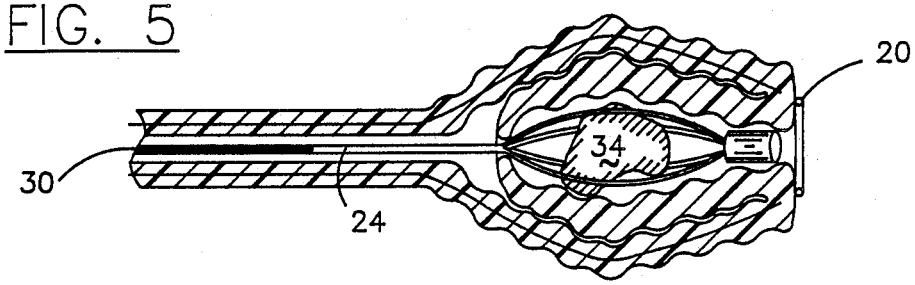
FIG. 5 is a view similar to FIG. 4 wherein the wire snare and kidney stone are enclosed within the distal end of the catheter of the present invention.

Referring now to FIGS. 3-8, the use of the catheter 10 of the present invention will be explained. As shown in FIG. 3, the catheter 10 with or without the snare means 22 disposed therein is inserted into a body passage to a point where an obstruction, such as a kidney stone 34, is located. At this point, the snare means 22 is manipulated in a manner to engage and capture the stone 34 (see FIG. 4). With the stone 34 captured and held by the capturing head 26, the elongated tube 24 which is affixed to the capturing head 26 is pulled outwardly. In performing this action, the cuff portion 12 of the catheter 10 begins to collapse axially inwardly into itself so as to form a double-layered sheath portion 36 which all but covers the capturing head 26 and the stone 34 held thereby as shown in FIG. 5. As will be clear to those skilled in the art, alternatively, the same function may be performed by holding the snare means 22 in position while advancing the catheter 10 inwardly.

Figure 6:
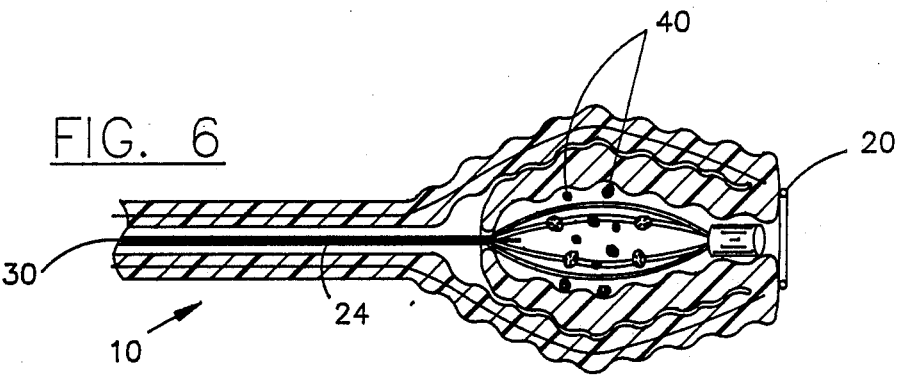
FIG. 6 is a view similar to FIG. 5 showing the use of a laser fiber for disintegrating the kidney stone.
Figure 7:
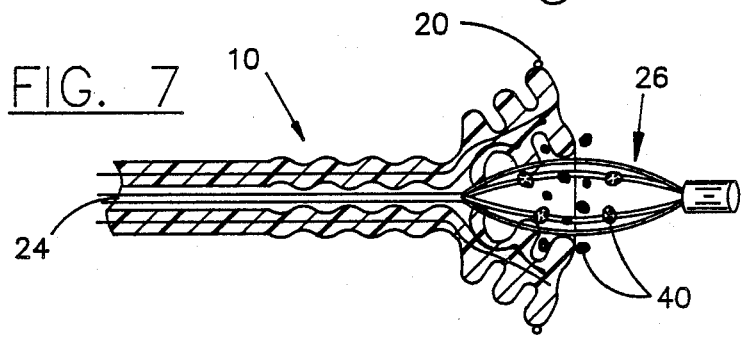
FIG. 7 is a view similar to FIG. 6 wherein the wire snare is being pushed out from the distal end of the catheter.
Figure 8:
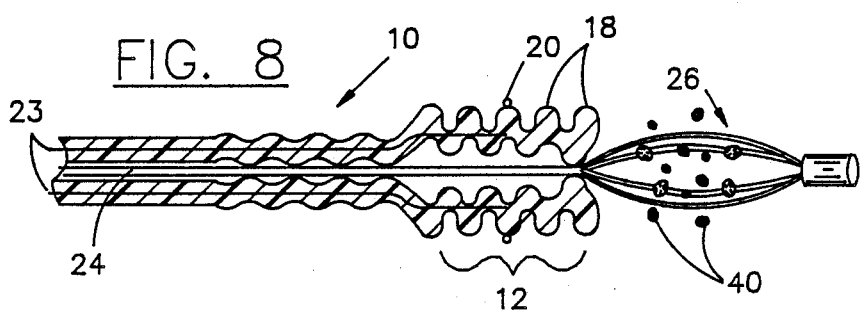
FIG. 8 is a view similar to FIG. 3.

With the stone 34 and capturing head 26 enveloped by the turned-in cuff portion 12, stone disintegration means such as a laser fiber 36 is inserted into the tube 24 to a position where it can be used to disintegrate the stone 34 into small fragments 40 as shown in FIG. 6.

Once the stone 34 has been disintegrated, the catheter 10 may be withdrawn from the body passage in its closed position with the fragment 40 held therein, or the catheter may be returned to its original configuration whereby the fragments 40 are released from the turned-in cuff portion 12. In the latter situation, the catheter 10 is simply withdrawn from the body opening and the fragments 40 are ultimately washed out of the body by normal body fluids.

As will be clear to those skilled in the art, other stone disintegration methods such as ultrasound, electrohydraulic lithotripsy, etc. may be employed in the tube 24. In the case where a laser is employed, the outer surface of the cuff portion 12 is preferably coated with a laser-reflective coating such as a powdered aluminum. A typical formulation would be powdered aluminum dispersed in an elastomer solution such as a silicone rubber.

The catheter 10 and the second elongated tube 24 of the present invention may be made from any suitable synthetic plastic material such as polyethylene, polyvinyl chloride, etc. Said material should be stiff enough to provide for insertion into a body opening without collapsing, yet flexible enough to permit it to conform to the body passage. In addition, the material selected for the catheter must be capable of being expanded or modified so as to form the inwardly collapsable cuff portion 12 for enveloping the capturing head 26 and kidney stone 34 as shown in FIGS. 4–6.

While only certain preferred features of the present invention have been shown by way of illustration, modifications and changes will occur to those skilled in the art.

What is claimed is:

1. A catheter device for capturing and holding kidney stones and the like within a body passage said device comprising in combination an elongated tube for insertion into a body passage said tube having distal and proximal ends wherein the length of said tube is such that said distal end is disposed within said body passage and said proximal end is disposed outside of said body passage; an axially inwardly collapsable cuff portion disposed adjacent the distal end of said tube, said cuff portion being an expanded portion of said tube wall and terminating in a free end; and snare means disposed within said tube and movable axially therein, said snare means comprising a second hollow elongated tube having a capturing head disposed at its distal end, said capturing head being disposed about the opening of said second hollow elongated tube wherein said capturing head with a kidney stone or the like held therein when moved outwardly of said body passage towards said expanded portion causes the free end of said cuff portion of said elongated tube to collapse axially inwardly into said expanded portion so as to envelope said capturing head and kidney stone or the like.

2. The catheter device of claim 1 wherein said cuff portion has corrugations formed in the outer surface thereof.

3. The catheter device of claim 2 wherein the wall of said elongated tube is provided with stiffening means which extends from said proximal end to a position which is about the midpoint of said cuff portion.

4. The catheter device of claim 3 wherein said stiffening means comprises at least one wire filament molded into the wall of said elongated tube.

5. The catheter device of claim 4 wherein said cuff portion means disposed about the circumference of said cuff portion to aid in the inward axial collapse of said cuff portion.

6. The catheter device of claim 1 further including kidney stone disintegrating means disposed in said second elongated tube.

7. The catheter device of claim 6 wherein said stone disintegrating means is an optical fiber for transmitting laser energy.

8. The catheter device of claim 7 wherein the outside surface of said cuff portion is coated with a laser-reflective coating.

9. The catheter device of claim 1 wherein said elongated tube is comprised of polyvinyl chloride.

* * * * *